(12) United States Patent
DeLuca et al.

(10) Patent No.: US 7,893,043 B2
(45) Date of Patent: Feb. 22, 2011

(54) 2-METHYLENE-(17Z)-17(20)-DEHYDRO-19,21-DINOR-VITAMIN D ANALOGS

(75) Inventors: Hector F. DeLuca, Deerfield, WI (US);
Bulli Padmaja Tadi, Madison, WI (US);
Lori A. Plum, Arena, WI (US);
Margaret Ciagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 14 days.

(21) Appl. No.: 12/171,071

(22) Filed: Jul. 10, 2008

(65) Prior Publication Data

US 2010/0009942 A1    Jan. 14, 2010

(51) Int. Cl.
*A61K 31/59* (2006.01)
*C07C 401/00* (2006.01)

(52) U.S. Cl. .................................. 514/167; 552/653
(58) Field of Classification Search .............. 514/167; 552/653
See application file for complete search history.

(56) References Cited

U.S. PATENT DOCUMENTS

| | | | |
|---|---|---|---|
| 4,666,634 | A | 5/1987 | Miyamoto et al. |
| 5,086,191 | A | 2/1992 | DeLuca et al. |
| 5,536,713 | A | 7/1996 | DeLuca et al. |
| 5,545,633 | A | 8/1996 | Bretting |
| 5,585,369 | A | 12/1996 | DeLuca et al. |
| 5,843,928 | A | 12/1998 | DeLuca et al. |
| 5,929,056 | A | 7/1999 | Mouriño et al. |
| 5,945,410 | A | 8/1999 | DeLuca et al. |
| 6,316,642 | B1 | 11/2001 | DeLuca et al. |

(Continued)

FOREIGN PATENT DOCUMENTS

WO    WO 94/01398    1/1994

(Continued)

OTHER PUBLICATIONS

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

(Continued)

*Primary Examiner*—Sabiha Qazi
(74) *Attorney, Agent, or Firm*—Andrus, Sceales, Starke & Sawall, LLP

(57) ABSTRACT

This invention discloses 2-methylene-(17Z)-17(20)-dehydro-19,21-dinor-vitamin D analogs, and specifically 2-methylene-(17Z)-17(20)-dehydro-19,21-dinor-1α, 25-dihydroxyvitamin $D_3$, and pharmaceutical uses therefor. This compound exhibits relatively high transcription activity as well as pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has significant calcemic activity in vivo having about the same bone calcium mobilization activity and intestinal calcium transport activity as the native hormone 1α,25-dihydroxyvitamin $D_3$, and therefore may be used to treat autoimmune disorders or inflammatory diseases in humans as well as renal osteodystrophy. This compound may also be used for the treatment or prevention of obesity.

79 Claims, 5 Drawing Sheets

U.S. PATENT DOCUMENTS

| | | | |
|---|---|---|---|
| 6,399,797 | B1 | 6/2002 | Von Daehne et al. |
| 6,537,981 | B2 | 3/2003 | DeLuca et al. |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 6,939,868 | B2 | 9/2005 | DeLuca et al. |
| 6,992,074 | B2 | 1/2006 | DeLuca et al. |
| 7,094,916 | B2 | 8/2006 | DeLuca et al. |
| 7,241,752 | B2 * | 7/2007 | DeLuca et al. ............. 514/167 |
| 2004/0220418 | A1 | 11/2004 | DeLuca et al. |

FOREIGN PATENT DOCUMENTS

| | | |
|---|---|---|
| WO | WO 98/24762 | 6/1998 |
| WO | WO 99/18070 | 4/1999 |
| WO | WO 2005/051323 | 6/2005 |

OTHER PUBLICATIONS

Darwish et al, "Identification of Transcription Factor That Binds to the Promoter Region of the Human Parathyroid Hormone Gene," Archives of Biochemistry and Biophysics, vol. 365, No. 1, pp. 123-130, (1999).

DeLuca, H.F. "*Therapeutic Potential of the 2-Alkyl and 2-Alkylidene-19-Nor-(20S)Modified Analogs of 1 α,25-Dihydroxyvitamin $D_3$,*" May 1, 2004, Journal of Steroid Biochemistry and Molecular Biology, Elsevier Science Ltd., Oxford, vol. 89/90, No. 1-5.

Lythgoe et al, "Calciferol and its Relatives. Part22. A Direct Total Synthesis of Vitamin $D_2$ and Vitamin $D_3$," J. Chem. Soc. Perkin Trans. 1, p. 590, (1978).

Lythgoe, "Synthetic Approaches to Vitamin D and its Relatives," Chem. Soc. Rev. 9, p. 449, (1983).

Miyamoto et al, "Synthetic Studies of Vitamin D Analogues. XIV. Synthesis and Calcium Regulating Activity of Vitamin $D_3$ Analogues Bearing a Hydroxyalkoxy Group at the 2β-Position," Chem. Pharm. Bull., vol. 41 No. 6, pp. 1111-1113, (1993).

Nishii et al, "The Development of Vitamin $D_3$ Analogues for the Treatment of Osteoporosis," Osteoporosis Int., Suppl. 1, pp. S190-S193, (1993).

Okano et al, "Regulatory Activities of 2β-(3-Hydroxypropoxy)-1α,25-Dihydroxy-Vitamin $D_3$, a Novel Synthetic Vitamin $D_3$ Derivative, on Calcium Metabolism," Biochemical and Biophysical Research Communications, vol. 163 No. 3, pp. 1444-1449, (1989).

Ostrem et al, "24- and 26-homo-1,25-dihydroxyvitamin $D_3$: Preferential activity in inducing differentiation of human leukemia cells HL-60 in vitro," Proc. Natl. Acad. Sci. USA, vol. 84, pp. 2610-2614, (1987).

Perlman et al, "1α,25-Dihydroxy-19-Nor-Vitamin $D_3$. A Novel Vitamin D-Related Compound with Potential Therapeutic Activity," Tetrahedron Letters, vol. 31 No. 13, pp. 1823-1824, (1990).

Perlman et al, "Novel Synthesis of 19-Nor-Vitamin D Compounds," Tetrahedron Letters, vol. 32 No. 52, pp. 7663-7666, (1991).

Posner et al, "Stereocontrolled Total Synthesis of Calcitriol Derivatives: 1,25-Dihydroxy-2-(4'-hydroxybutyl)vitamin $D_3$ Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin $D_3$. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Sardina et al, "Studies on the Synthesis of Side-Chain Hydroxylated Metabolites of Vitamin D.2. Stereocontrolled Synthesis of 25-Hydroxyvitamin $D_2$," J. Org. Chem., 51, pp. 1264-1269, (1986).

Toh et al, "Studies on a Convergent Route to Side-Chain Analogues of Vitamin D: 25-Hydroxy-23-Oxavitamin $D_3$ ,"J. Org. Chem., 48, 1414, (1983).

* cited by examiner

2-METHYLENE-(17Z)-17(20)-DEHYDRO-19,21-DINOR-VITAMIN D ANALOGS

BACKGROUND OF THE INVENTION

This invention relates to vitamin D compounds, and more particularly to 2-methylene-(17Z)-17(20)-dehydro-19,21-dinor-vitamin D analogs and their pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

17-ene vitamin D compounds as well as vitamin D compounds having a double bond in the side chain thereof are also known, and have been proposed for various pharmacological uses. Bone diseases such as osteoporosis, skin disorders such as psoriasis, cancers such as leukemia and cosmetic conditions such as wrinkles are just some of the applications proposed for such compounds. 17-ene compounds are described in U.S. Pat. Nos. 5,545,633; 5,929,056 and 6,399,797 while 2-alkylidene compounds having a side chain with a double bond therein are described in, for example, U.S. Pat. No. 5,843,928.

SUMMARY OF THE INVENTION

The present invention is directed toward 2-methylene-(17Z)-17(20)-dehydro-19,21-dinor-vitamin D analogs, their biological activity, and various pharmaceutical uses for these compounds. These new vitamin D compounds not known heretofore are the 19-nor-vitamin D analogs having a methylene group at the 2-position (C-2), a double bond located between carbon atoms 17 and 20, the replacement of the methyl group typically located at the 21 position (C-21) in the side chain with a hydrogen atom, and the side chain attached at the 17-position (C-17) in its Z-configuration. The preferred vitamin D analog is 2-methylene-(17Z)-17(20)dehydro-19,21-dinor-1α,25-dihydroxyvitamin $D_3$ (hereinafter referred to as "Vit II Z").

Structurally these 2-methylene-(17Z)-17(20)-dehydro-19,21-dinor-vitamin D analogs are characterized by the general formula I shown below:

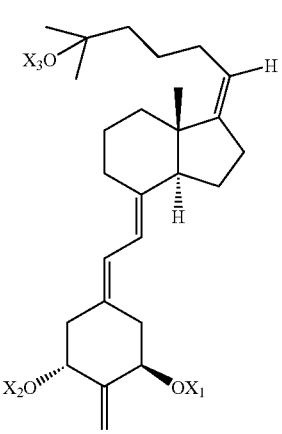

where $X_1$, $X_2$ and $X_3$, which may be the same or different, are each selected from hydrogen or a hydroxy-protecting group. The preferred analog is 2-methylene-(17Z)-17(20)-dehydro-19,21-dinor-1α,25-dihydroxyvitamin $D_3$ which has the following formula Ia:

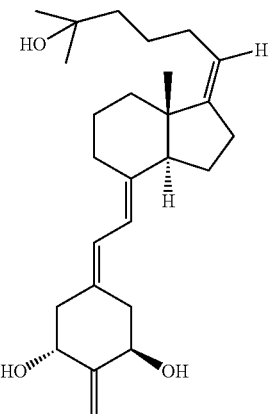

Ia

The above compounds I, particularly Ia, exhibit a desired, and highly advantageous, pattern of biological activity. These compounds are characterized by relatively high binding to vitamin D receptors, which is only slightly lower potency than that of the natural hormone 1α,25-dihydroxy vitamin D$_3$. These compounds also have the ability to promote intestinal calcium transport in vivo, in a dose dependent manner, and they would be classified as having about the same or equal intestinal calcium transport activity, as compared to that of 1α,25-dihydroxyvitamin D$_3$. These compounds I, and particularly Ia, also have the ability to mobilize calcium from bone and they would be classified as having about the same or equal bone calcium mobilizing activity, as compared to 1α,25-dihydroxyvitamin D$_3$. Hence, these compounds can be characterized as having significant calcemic activity. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having calcemic activity while also very active on differentiation and transcription are expected to be useful as a therapy for suppression of secondary hyperparathyroidism of renal osteodystrophy.

The compounds I, particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity and in promoting transcription. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIG. 1 is a graph illustrating the relative activity of Vit II Z and 1,25(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of Vit III Z and 1,25(OH)$_2$D$_3$;

FIG. 3 is a graph illustrating the in vitro transcription activity of 1,25(OH)$_2$D$_3$ as compared to Vit II Z;

FIG. 4 is a graph illustrating the bone calcium mobilization activity of 1,25(OH)$_2$D$_3$ as compared to Vit II Z; and FIG. 5 is a graph illustrating the intestinal calcium transport activity of 1,25(OH)$_2$D$_3$ as compared to Vit II Z.

Figure 1:
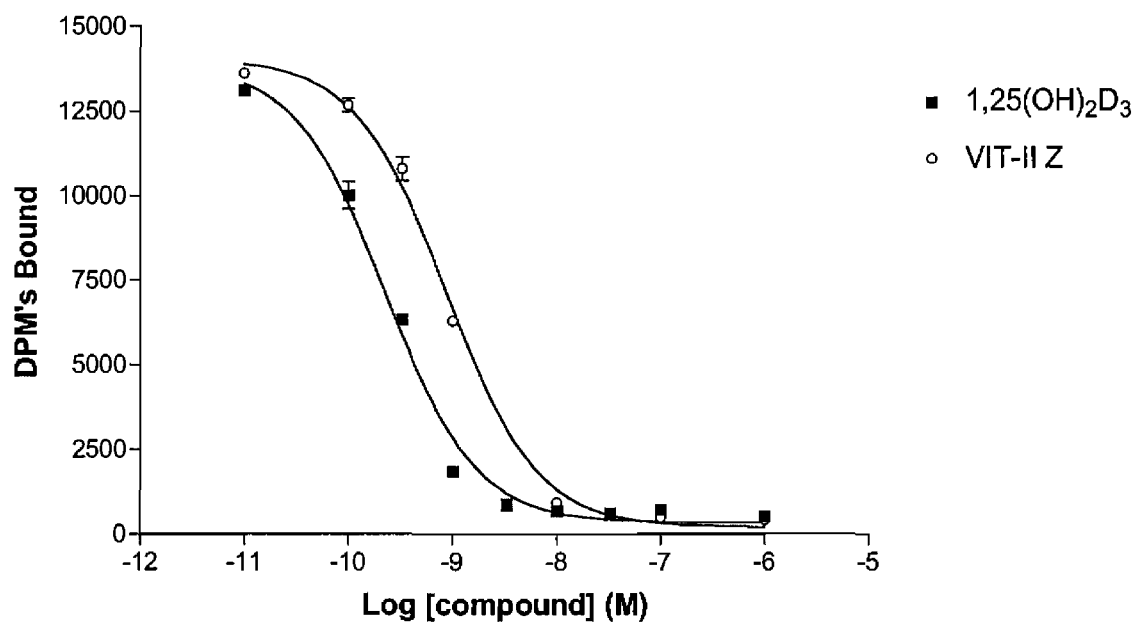
FIGS. 1-5 illustrate various biological activities of 2-methylene-(17Z)-17(20)-dehydro-19,21-dinor-1α,25-dihydroxyvitamin D$_3$, hereinafter referred to as "Vit II Z," as compared to the native hormone 1α,25-dihydroxyvitamin D$_3$, hereinafter "1,25(OH)$_2$D$_3$."

DETAILED DESCRIPTION OF THE INVENTION 2-methylene-(17Z)-17(20)-dehydro-19,21-dinor-1α,25-dihydroxyvitamin D$_3$ (referred to herein as "Vit II Z") a 19-nor vitamin D analog which is characterized by the presence of a methylene substituent at the carbon 2 (C-2), a double bond located between carbon atoms 17 and 20, the replacement of the methyl group typically located at the 21-position (C-21) in the side chain with a hydrogen atom, and the side chain attached at the 17-position (C-17) in its Z-configuration, was synthesized and tested. Such vitamin D analog seemed an interesting target because the relatively small methylene group at the C-2 position should not interfere with binding to the vitamin D receptor. Structurally, this 19-nor analog is characterized by the general formula Ia previously illustrated herein, and its pro-drug (in protected hydroxy form) is characterized by general formula I previously illustrated herein.

The preparation of 2-methylene-(17Z)-17(20)-dehydro-19,21-dinor-vitamin D analogs having the structure I can be accomplished by a common general method, i.e. the condensation of a bicyclic Windaus-Grundmann type ketone II with the allylic phosphine oxide III to the corresponding 2-methylene-19,21-dinor-vitamin D analog IV followed by deprotection at C-1 and C-3 in the latter compound (see the Scheme herein):

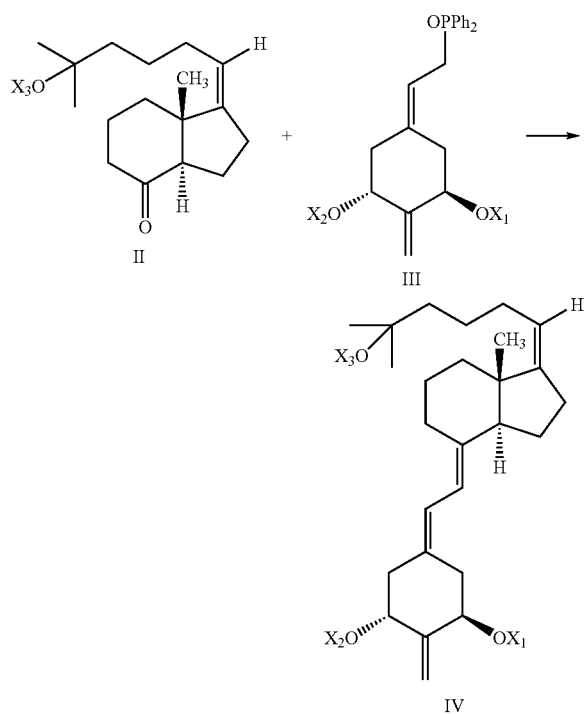

In the structures II, III and IV, groups $X_1$, $X_2$ and $X_3$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown in the Scheme herein (see the preparation of compound Vit II Z).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following illustrative example and description as well as to the Scheme herein for a detailed illustration of the preparation of compound Vit II Z.

In this example specific products identified by Arabic numerals (1, 2, 3) refer to the specific structures so identified in the Scheme.

EXAMPLE

Chemistry. Ultraviolet (UV) absorption spectra were recorded with a Hitachi Model 60-100 UV-vis spectrometer in the solvent noted. $^1$H nuclear magnetic resonance (NMR) spectra were recorded at 500 MHz with a Bruker AM-500 FT spectrometer in deuteriochloroform. Chemical shifts (δ) are reported downfield from internal Me$_4$Si (δ0.00). Mass spectra were recorded at 70 eV on a Kratos DS-50 TC instrument equipped with a Kratos MS-55 data system. Samples were introduced into the ion source maintained at 120-250° C. via a direct insertion probe. High-performance liquid chromatography (HPLC) was performed on a Waters Associates liquid chromatograph equipped with a Model 6000A solvent delivery system, a Model 6 UK Universal injector, a Model 486 tunable absorbance detector, and a differential R 401 refractometer.

Example 1

Des-A,B-23,24-dinorcholan-8β,22-diol (2). A flame dried 1000 mL two necked flask was charged with ergocalciferol 1 (5 g, 12.6 mmol), pyridine (5 mL), and anhydrous MeOH (400 mL). The solution was cooled to −78° C. in an argon atmosphere. O$_3$ was bubbled through the solution until a deep blue colour developed and persisted (about 1 h). The solution was treated with $O_2$ until the blue colour faded (15 min). Then $NaBH_4$ (1.5 g, 39.7 mmol) was added. After 15 min. second portion of $NaBH_4$ (1.5 g, 39.7 mmol) was added and the reaction was allowed to warm to rt. Then the third portion of $NaBH_4$ (1.5 g, 39.7 mmol) was added and reaction stirred for over night. The reaction was quenched by adding water (50 mL). Methanol was evaporated in vaccuo and residue was dissolved in ethyl acetate. The organic phase was washed with 1N aqueous solution of HCl (100 mL), saturated $NaHCO_3$ solution (100 mL) and brine (100 mL). The organic phase was dried ($Na_2SO_4$), filtered and evaporated. Purification by silica gel chromatography (25% ethyl acetate/hexane) afforded 2.18 g (10.3 mmol, 81%) of diol 2 as a white solid. Mp 110-111° C.; $^1$H NMR (400 MHz, $CDCl_3$)δ: 0.96 (3H, s), 1.03 (3H, d, J=6.6 Hz), 3.38 (1H, dd, J=10.5, 6.7 Hz), 3.64 (1H, dd, J=10.5, 3.2 Hz), 4.09 (1H, m); $^{13}$C NMR (100 MHz, $CDCl_3$) δ: 69.2, 67.8, 52.9, 52.4, 41.8, 40.2, 38.2, 33.6, 26.6, 22.6, 17.4, 16.6, 13.6; MS m/z (relative intensity): 212 ($M^+$, 2), 194 ($M^+-H_2O$, 15), 179 ($M^+-H_2O-CH_3$, 18), 125 (43), 111 (100); exact mass calculated for $C_{13}H_{22}O$ $[M-H_2O]^+$ is 194.1671, measured is 194.1665.

Des-A,B-22-(p-toluenesulfonyloxy)-23,24-dinorcholan-8β-ol (3). A solution of diol 2 (1 g, 4.71 mmol) in anhydrous pyridine (12 mL) was cooled to −25° C. and a precooled solution of tosyl chloride (1.08 g, 5.66 mmol) in anhydrous pyridine (2 mL) was added dropwise. The reaction mixture was stirred at that temperature for 4 h and allowed to warm to 0° C. and stirred at that temperature for additional 20 h. The mixture was diluted with $CH_2Cl_2$ (50 mL) and washed with saturated $CuSO_4$ solution (30 mL), 1N HCl (30 mL), and water (50 mL). The organic phase was dried ($NaSO_4$), filtered and concentrated. Purification by silica gel chromatography (25% ethyl acetate/hexane) yielded 1.7 g (4.64 mmol, 98%) of hydroxyl tosylate 3. $^1$H NMR (400 MHz, $CDCl_3$) δ: 0.89 (3H, s), 0.96 (3H, d, J=6.6Hz), 2.45 (3H, s), 3.8 (1H, dd, J=9.2, 6.2 Hz), 3.95 (1H, dd, J=9.2, 3.0 Hz), 4.06 (1H, m), 7.35 (2H, d, J=8.2 Hz), 7.78 (2H, d, J=8.2 Hz); $^{13}$C NMR (100 MHz, $CDCl_3$) δ: 144.7, 133.0, 129.8, 127.9, 75.6, 69.0, 60.4, 52.2, 41.9, 40.1, 35.7, 33.5, 26.4, 22.4, 21.6, 17.3, 16.7, 13.4; MS m/z (relative integration): 366 ($M^+$, 6), 194(14), 179(16), 125(30), 111(100); exact mass calculated for $C_{20}H_{30}SO_4Na$ $(M+Na^+)$ is 389.1763, measured is 389.1768.

Des-A,B-8β-[(triethylsilyl)oxy]-22-(p-toluenesulfonyloxy)-23,24-dinorcholane (4). To a −50° C. cooled solution of hydroxyl tosylate 3 (1.5 g, 4.09 mmol) in anhydrous CH2Cl2 (20 mL) was added 2,6-lutidine (0.950 mL, 0.880 g, 8.2 mmol) followed by TESOTf (1.4 mL, 1.6 g, 6.14 mmol). The solution was stirred at −50° C. for 15 min and water (10 mL) was added. The mixture was extracted with $CH_2Cl_2$ (3×40 mL), and combined organic phases were washed with 1N aqueous solution of NaOH (40 mL) dried ($Na_2SO_4$), filtered and concentrated. The residue was purified by silica gel column chromatography (5% ethyl acetate/hexane) to give 1.7 g (3.54 mmol, 86%) of 4. $^1$H NMR (400 MHz, $CDCl_3$) δ: 0.53 (6H, q, J=7.9 Hz), 0.86 (3H, s), 0.93 (9H, t, J=7.9 Hz), 0.94 (3 H, d, J=7 Hz) 2.43 (3H, s), 3.78 (1H, dd, J=9.2, 6.4 Hz), 3.95 (1H, dd, J=9.2, 3.0 Hz), 4.0 (1H, m), 7.33 (2H, d, J=8.0 Hz), 7.77 (2H, d, J=8.2 Hz). $^{13}$C NMR (100 MHz, $CDCl_3$) δ: 144.5, 133.1, 129.7, 127.9, 75.7, 69.1, 52.7, 52.4, 42.1, 40.3, 35.7, 34.5, 26.5, 22.9, 21.6, 17.5, 16.7, 13.4, 6.9, 4.9; MS m/z (relative integration): 480 ($M^+$, 30), 437(50), 327(18), 257 (90), 177(100); exact mass calculated for $C_{26}H_{44}O_4SSiNa$ $(M+Na^+)$ is 480.2730, measured is 480.2741.

Des-A,B-8β-[(triethylsilyl)oxy]-23,24-dinorcholan-22-al (5). A solution of 4 (1.5 g, 3.12 mmol) in DMSO (5 mL) was added to a suspension of $NaHCO_3$ (1.3 g, 15.6 mmol) in DMSO (20 mL) at rt. The mixture was heated to 150° C. under argon for 15 min and cooled to rt. Water (50 mL) followed by ethyl acetate (50 mL) were added and aqueous phase was extracted with ethyl acetate (3×30 mL). The combined organic phases were dried ($Na_2SO_4$), filtered and concentrated. The residue was purified by column chromatography (2% ethyl acetate/hexane) to afford 0.770 g (2.38 mmol, 76%) of aldehyde 5. $^1$H NMR (500 MHz, $CDCl_3$) δ: 0.56 (6H, q, J=8.0 Hz), 0.95 (9H, t, J=7.9 Hz), 0.96 (3H, s) 1.1 (3H, d, J=6.8 Hz), 4.06 (1H, m), 9.58 (1H, d, J=3.2 Hz). $^{13}$C NMR (100 MHz, $CDCl_3$) δ: 205.5, 69.0, 52.4, 51.7, 49.1, 42.6, 40.5, 34.5, 26.2, 23.3, 17.6, 13.9, 13.3, 6.9, 4.9; MS m/z (relative integration): 295 ($[M-C_2H_5]^+$, 40), 265(3), 163(100); exact mass calculated for $C_{17}H_{31}SiO_2(M-C_2H_5^+)$ is 295.2093, measured is 295.2095.

Des-A,B-8β-[(triethylsilyl)oxy]-pregnan-20-one (6). A flame dried flask was charged with t-BuOK (1.35 g, 11.9 mmol) and anhydrous t-BuOH (30 mL) at room temperature. $O_2$ was bubbled through the solution for 15 min. A solution of aldehyde 5 (0.770 g, 2.38 mmol) in anhydrous t-BuOH (15 mL) was added to the reaction mixture and $O_2$ was bubbled through the solution for additional 10 min. The reaction was quenched with water (15 mL) and extracted with ether (3×30 mL). The combined organic phases were dried ($Na_2SO_4$), filtered and concentrated. The residue was purified by column chromatography (3% ethyl acetate/hexane) to give 0.520 g (1.68 mmol, 71%) of the ketone 6. $^1$H NMR (500 MHz, $CDCl_3$) δ: 0.55 (6H, q, J=7.9 Hz), 0.85 (3H, s), 0.94 (9H, t, J=8.0 Hz), 2.09 (3H, s), 4.07 (1H, m). $^{13}$C NMR (100 MHz, $CDCl_3$) δ: 209.6, 68.9, 64.5, 53.2, 43.7, 39.9, 34.4, 31.5, 23.1, 21.7, 17.6, 15.3, 6.9, 4.9; MS m/z (relative integration): 310 ($M^+$, 13), 295(3), 281(100); exact mass calculated for $C_{18}H_{34}SiO_2$ $(M^+)$ is 310.2328, measured is 310.2325.

Des-A,B-8β-[(triethylsilyl)oxy]-testosterone acetate (7). To a 0° C. cooled solution of ketone 6 (0.610 g, 1.97 mmol) in $CH_2Cl_2$ (10 mL) was added m-CPBA (77%, 1.0 g, 3.94 mmol) and stirred at room temperature for 6 days [additional amounts of m-CPBA were added (1.0 g, 48 h; 0.400 g 96 h)]. The reaction mixture was diluted with $CH_2Cl_2$ (30 mL) and washed with saturated aqueous solution of $NaHCO_3$ (30 mL). The aqueous phase was extracted with $CH_2Cl_2$ (2×20 mL). The combined organic phases were washed with water (20 mL), dried ($Na_2SO_4$) and concentrated. The residue was purified by column chromatography (2% ethyl acetate/hexane) to give 0.400 g, (1.23 mmol, 62%) of acetate 7 as white solid. $^1$H NMR (400 MHz, $CDCl_3$) δ: 0.56 (6H, q, J=7.95 Hz), 0.95 (9H, t, J=7.97 Hz), 1.0 (3H, s), 2.03 (3H, s), 4.05 (1H, m), 4.54 (1H, t, J=8.1 Hz). MS m/z (relative integration): 326 ($M^+$, 8), 297 ($[M-C_2H_5]^+$, 32), 281 (27) 135(100); exact mass calculated for $C_{18}H_{34}O_3Si$ $(M^+)$ is 326.2277, measured is 326.2262.

Des-A,B-8β-[(triethylsilyl)oxy]-testosterone (8). To a ice cooled solution of acetate 7 (0.400 g, 1.23 mmol) in MeOH (9 mL) and $H_2O$ (1 mL) was added NaOH (0.490 g, 12.3 mmol). The resulting mixture was stirred at room temperature for 6 hrs. The resulting solution was treated with an aqueous solution of $NH_4Cl$ (10 mL). MeOH was removed in vacuo and aqueous phase was extracted with ethyl acetate (3×30 mL). The combined organic phases were dried filtered and concentrated. The residue was purified by column chromatography (10% ethyl acetate/hexane) to yield 0.290 g (1.02 mmol, 83%) of alcohol 8 as a white solid. $[\alpha]^{20}_D$+38.94 (c 0.64, $CHCl_3$); $^1$H NMR (400 MHz, $CDCl_3$) δ: 0.56 (6H, t, J=7.9 Hz), 0.95 (9H, t, J=7.96 Hz), 0.96 (3H, s), 2.04 (1H, m), 3.56 (1H, t, J=7.68 Hz), 4.02 (1H, m). $^{13}$C NMR (100 MHz, $CDCl_3$) δ: 82.2, 69.1, 48.1, 42.1, 37.5, 34.6, 29.9, 22.1, 17.3, 12.3, 6.9, 4.9 . MS m/z (relative intensity): 284 ($M^+$, 12), 255([M-CH$_3$—H$_2$O]$^+$, 100) 237(52), 135(50). Exact mass calculated for C$_{16}$H$_{32}$O$_2$Si [M]$^+$ is 284.2172, found 284.2166.

Des-A,B-8β-[(triethylsilyl)oxy]-androstane-17-one (9). To an ice cooled solution of alcohol 8 (0.290 g, 1.02 mmol) in dry CH$_2$Cl$_2$ (10 mL) was added PDC (0.576 g, 1.53 mmol). The reaction mixture was stirred at room temperature over night and filtered through celite. The solution was concentrated and purified by column chromatography (7% ethyl acetate/ hexane) to yield 0.256 g (0.91 mmol, 89%) of ketone 9 as colourless liquid. [α]$^{20}_D$+80.4 (c 0.92, CHCl$_3$); $^1$H NMR (400 MHz, CDCl$_3$) δ: 0.58 (6H, t, J=8.05 Hz), 0.95 (9H, t, J=7.95 Hz), 1.09 (3H, s), 2.41 (1H, m), 4.17 (1H, m). $^{13}$C NMR (100 MHz, CDCl$_3$) δ: 82.2, 69.8, 48.8, 47.5, 35.2, 34.4, 32.2, 21.2, 16.9, 16.1, 6.8, 4.9 . MS m/z (relative intensity): 282 (M$^+$, 23), 253([M-CH$_3$—H$_2$O]$^+$, 100) 171(12). Exact mass calculated for Cl$_{16}$H$_{30}$O$_2$Si [M]$^+$ is 282.2015, found 282.2012.

(17Z)-Des-A,B-8β-[(triethylsilyl)oxy]-21,26,27-trinorcholest-17(20)-ene-25-oic Acid (11): To a solution of t-BuOK (0.895 g, 7.98 mmol) in anhydrous benzene (15 mL) was added (4-carboxybutyl)triphenylphosphonium bromide (1.180 g, 2.66 mmol) in benzene (10 mL) under argon atmosphere. The reaction mixture was refluxed for one hour and then a solution of ketone 9 (0.250 g, 0.89 mmol) in benzene (5 mL) was added. After refluxing the solution for 24 h the mixture was washed with water and the aqueous phase was acidified with HCl (10%) and extracted with ethyl acetate (3×10 mL). The combined organic phase was dried, filtered and concentrated. The residue was purified by column chromatography (16% ethyl acetate/hexane) to yield 0.191 g (0.52 mmol, 59%) of acid 11 as yellow oil. [α]$^{20}_D$+2.77 (c 0.79, CHCl$_3$); $^1$H NMR (400 MHz, CDCl$_3$) δ: 0.56 (6H, q, J=7.96 Hz), 0.95 (9H, t, J=7.92 Hz), 1.08 (3H, s), 4.1 (1H, m), 4.9 (1H, t, J=7.36 Hz). $^{13}$C NMR (100 MHz, CDCl$_3$) δ: 180.1, 151.3, 117.5, 69.6, 52.7, 44.2, 38.2, 34.5, 33.6, 30.6, 26.7, 25.6, 23.6, 19.9, 17.9, 6.9, 4.9 . MS m/z (relative intensity): 366 (M$^+$, 3), 351([M-CH$_3$]$^+$, 2) 234(100). Exact mass calculated for C$_{21}$H$_{37}$O$_3$Si [M-H]$^-$ is 365.2512, found 365.2518.

(17Z)-Des-A,B-8β-[(triethylsilyl)oxy]-21-norcholest-17(20)-ene-25-ol (12): To a solution of compound (0.100 g, 0.27 mmol) in dry THF (10 mL) at 0° C. was added MeLi ((1.6M in Et$_2$O, 0.340 mL, 0.55 mmol) dropwise. The reaction mixture was stirred at room temperature for 2 h and quenched with ice. The mixture was extracted with diethyl ether (2×10 mL) and the combined extracts were washed dried, filtered and concentrated. The residue was purified by column chromatography (8% ethyl acetate/hexane) to yield 0.071 g (0.19 mmol, 69%) of methyl ester. To a solution of methyl ester (0.071 g, 0.19 mmol) in dry THF (5 mL) was added a solution of MeLi (1.6M in Et$_2$O, 0.340 ml, 0.56 mmol) at −78° C. After 1 h at −78° C. the reaction mixture was allowed to come to room temperature and stirred for additional 1 h. The reaction was quenched with ice and extracted with ethyl acetate (2×5 mL). The combined organic phases were dried, filtered and concentrated. The residue was purified by column chromatography (15% ethyl acetate/hexane) to yield 43 mg (0.11 mmol, 60%) of alcohol. $^1$H NMR (500 MHz, CDCl$_3$) δ: 0.56 (6H, q, J=7.89 Hz), 0.95 (9H, t, J=7.95 Hz), 1.09 (3H, s), 1.20 (6H, s), 2.39 (1H, dd, J=16.3 and 9.7 Hz), 4.1 (1H, d, J=1.6 Hz), 4.93 (1H, t, J=7.29 Hz). $^{13}$C NMR (125 MHz, CDCl$_3$) δ: 150.4, 118.8, 71.0, 69.7, 52.8, 44.2, 43.7, 38.3, 34.6, 30.6, 29.6, 29.2, 27.8, 25.5, 23.7, 19.9, 17.9, 6.9, 4.9.

(17Z)-Des-A,B-21-norcholest-17(20)-ene-8β,25-diol (13): A solution of silyl ether 12 (28 mg, 73.7 μmol) in dry THF (2 mL) was treated with TBAF (1 M in THF, 0.368 mL, 0.096 g, 0.37 mmol). The reaction mixture was stirred at room temperature for 12 h. The reaction was quenched with saturated NaHCO$_3$ solution and aqueous phase was extracted with diethyl ether (3×5 mL). The organic phases were dried filtered and concentrated. The residue was purified by column chromatography to afford 16 mg (82%, 60.1 μmol) of diol 13 . [α]$^{20}_D$−6.38 (c 0.79, CHCl$_3$); $^1$H NMR (400 MHz, CDCl$_3$) δ: 1.13 (3H, s), 1.20 (6H, m), 2.43 (1H, m), 4.15 (1H, m), 4.97 (1H, t, J=7.28 Hz). $^{13}$C NMR (100 MHz, CDCl$_3$) δ: 149.4, 119.3, 71.0, 69.2, 52.2, 43.7, 43.6, 37.9, 33.5, 30.4, 29.2, 27.7, 25.4, 23.2, 19.8, 17.7 . MS m/z (relative intensity): 266 (M$^+$, 3), 248([M-H$_2$O]$^+$, 8), 233([M-CH$_3$—H$_2$O]$^+$, 15), 147(100).

17(Z)-Des-A,B-25-(Triethylsilyloxy)-21-norcholestan-17(20)-ene-8-one (14). To a solution of alcohol 13 (16 mg, 60.1 μmol) in anhydrous CH$_2$Cl$_2$ (5 mL) was added PDC (34 mg, 90.2 μmol) at rt. After stirring the reaction for 3 h under argon atmosphere the solution was passed through a pad of celite with ethyl acetate. The filtrate was concentrated and applied on a Sep-Pak cartridge and eluted with ethyl acetate/hexane (20% ethyl acetate/hexane) to give 12 mg, (45.5 μmol, 76%) of ketone as colourless oil. To a −50° C. cooled solution of ketone (12 mg, 45.5 μmol) in anhydrous CH$_2$Cl$_2$ (5 mL) was added 2,6-lutidine (11 μL, 9.7 mg, 91 μmol) followed by TESOTf (16 μL, 18 mg, 68 μmol). The solution was stirred at −50° C. for 15 min and water (5 mL) was added. The mixture was extracted with CH$_2$Cl$_2$ (3×5 mL), and combined organic phases were washed with 1N aqueous solution of NaOH (10 mL) dried (Na$_2$SO$_4$), filtered and concentrated. The ketone was purified on HPLC (9.4-mm×25-cm Zorbax-Sil column, 4 ml/min) using 10% ethyl acetate/hexane solvent system. Pure ketone 14 11.6 mg (30.7 μmol, 68%) was eluted at R$_v$=20 mL as colorless oil. $^1$H NMR (400 MHz, CDCl$_3$) δ: 0.56 (6H, q, J =7.84 Hz), 0.86 (3H, s), 0.94 (9H, t, J=7.96 Hz), 1.19 (6H, s), 2.59 (1H, dd, J=12.28, 6.2 Hz). 5.12 (1H, t, J=7.40 Hz).

17(Z)-1α,25 Dihydroxy-17(20)-ene-2-methylene-19,21-dinorvitamin D$_3$ (17). To a solution of phosphine oxide 15 (0.047 g, 80.7 μmol) in anhydrous THF (500 μL) at −25° C. was slowly added PhLi 1.2M in cyclohexane/ether (70/30) (74 μL, 7.5 mg, 88.8 μmol) under argon with stirring. The solution turned deep orange. The mixture was stirred at that temperature for 20 min and cooled to −78° C. A precooled (−78° C.) solution of ketone 14 (11.6 mg, 30.7 μmol) in anhydrous THF (100 μL) was added slowly. The mixture was stirred under argon atmosphere at −78° C. for 3 h and at 0° C. for 18 h. Ethyl acetate was added and organic phase was washed with brine, dried (Na$_2$SO$_4$) and evaporated. The residue was applied on a Sep-Pak cartridge, and eluted with 1% ethyl acetate/hexane to give 19-nor protected vitamin derivative 16 . The protected vitamin was further purified by HPLC (9.4-mm×25-cm Zorbax-Sil column, 4 ml/min) using hexane/IPA (99.95/0.05) solvent system. Pure compound 16, 8.4 mg (11.4 μmol, 37%) was eluted at R$_v$=16 mL as colourless oil. UV (in hexane) λ$_{max}$ 243, 251.8, 262.2 nm; $^1$H NMR (400 MHz, CDCl$_3$) δ: 0.02, 0.05, 0.06, 0.08 (each 3H, each s), 0.56 (6H, q, J=7.6 Hz), 0.76 (3H, s), 0.86 and 0.90 (each 9H, each s), 0.96 (9H, t, J=8.0 Hz), 1.19 (6H, s), 2.19 (1H, m), 2.33 (1H, m) 2.47 (1H, dd, 12.9, 4.56 Hz), 2.53 (1H, dd, 13.3, 5.88 Hz), 2.81 (1H, m), 4.43 (2H, m), 4.93 and 4.98 (1H and 1H, each s), 5.09 (1H, t, J=7.3 Hz), 5.88 and 6.21 (1H and 1H, each d, J=11.2 Hz); MS m/z (relative intensity): No M$^+$, 610(20), 366(7), 103(100); Exact mass calculated for C$_{38}$H$_{67}$O$_2$Si$_2$ [M-C$_6$H$_{15}$SiO]$^+$ is 611.4680, found 611.4692.

The protected vitamin 16 (8.4 mg, 11.4 μmol) was dissolved in anhydrous THF (500 μL) and treated with TBAF (0.115 mL, 30 mg, 114 μmol) and stirred at rt in dark for overnight. The solvent was removed in vaccuo and residue was applied on Sep-Pak cartridge, and eluted with 30% ethyl acetate/hexane to get the deprotected vitamin 17. The vitamin was further purified by HPLC (9.4-mm×25-cm Zorbax-Sil column, 3 mL/min) using hexane/IPA (90/10) as solvent system. Pure vitamin 17, 3.1 mg (7 μmol, 70%) was collected at $R_v$=42 mL as white solid: UV (in EtOH) $\lambda_{max}$ 243, 251.8, 262.2 nm; $^1$H NMR (500 MHz, CDCl$_3$) δ: 0.76 (3H, s), 1.21 (6H, s), 2.30 (1H, dd, J=12.24, 7.9 Hz), 2.35 (1H, dd, J=13.0, 5.74 Hz), 2.58 (1H, dd, J=13.3, 3.8 Hz), 2.80 (1H, br d) 2.87(1H, dd, J=13.1, 4.4 Hz), 4.49 (2H, m), 5.07 (3H, m), 5.92 and 6.35 (1H and 1H, each d, J=11.09 Hz); MS m/z (relative intensity): 400 (M$^+$, 5), 367([M-H$_2$O—CH$_3$]$^+$, 1) 285(7), 249 (40) 192(100).

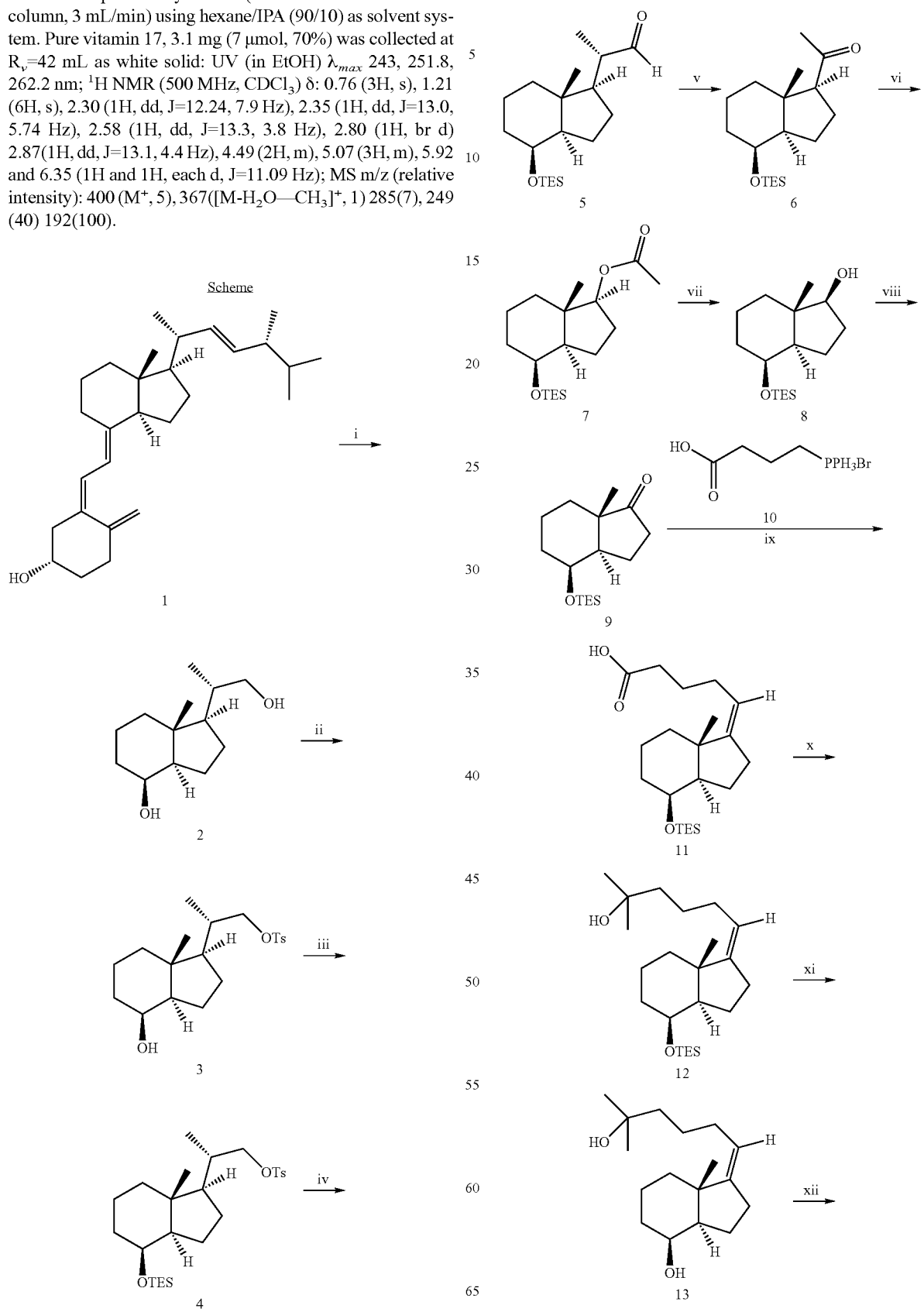

-continued

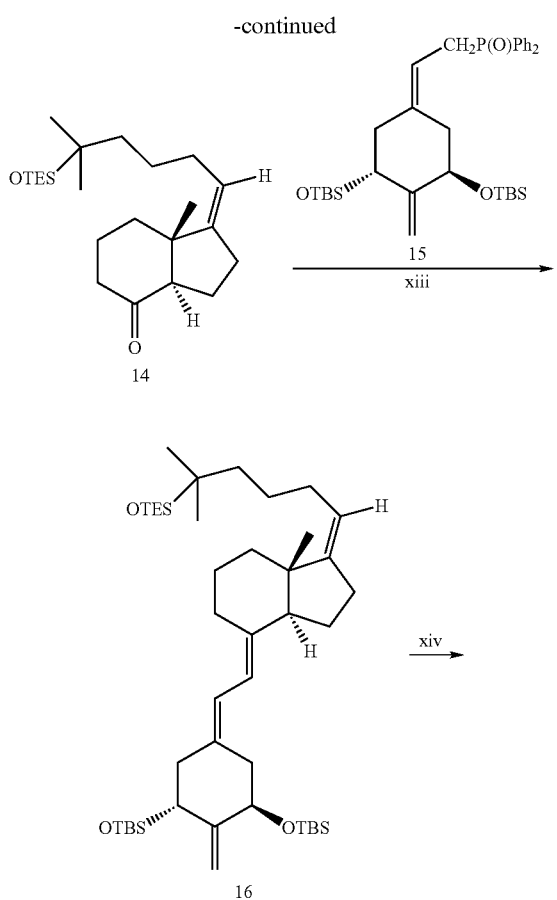

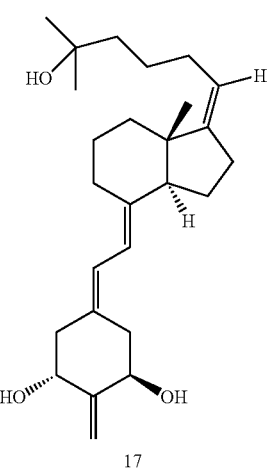

(i) $O_3$, $C_5H_5N$, MeOH, $NaBH_4$, 81%. (ii) TsCl, $C_5H_5$,N, 98%. (iii) TESOTf, 2,6-lutidine, $CH_2Cl_2$, 86% (iv) $NaHCO_3$, DMSO, 76% (v) t-BuOK, t-BuOH, $O_2$, 71%. (vi) mCPBA, $CH_2Cl_2$, 62% (vii) MeOH:$H_2O$ (9:1), NaOH, 83% (viii) PDC, $CH_2Cl_2$, 89% (ix) 10, t-BuOK, $C_6H_6$, 59% (x) MeLi, Diethyl ether, 0° C. 69%; MeLi, Diethyl ether −78° C., 60% (xi) TBAF, THF, 82% (xii) PDC, $CH_2Cl_2$, 76%; TESOTf, 2,6-lutidine, $CH_2Cl_2$, 68% (xiii) 15, PhLi, THF, 37% (xiv) TBAF, THF, 70%.

BIOLOGICAL ACTIVITY OF 2-METHYLENE-(17Z)-17(20)-DEHYDRO-19,21-DINOR-1α,25-DIHYDROXYVITAMIN $D_3$

The introduction of a methylene group to the 2-position, a double bond between carbon atoms 17 and 20, the replacement of the methyl group typically located at the 21 position (C-21) in the side chain with a hydrogen atom, and the side chain attached at the 17-position (C-17) in its Z-configuration, had little effect on binding of Vit II Z to the full length recombinant rat vitamin D receptor, as compared to 1α,25-dihydroxyvitamin $D_3$. The compound Vit II Z bound with nearly the same affinity to the nuclear vitamin D receptor as compared to the standard 1,25-$(OH)_2D_3$ (FIG. 1). It might be expected from these results that compound Vit II Z would have equivalent biological activity. Surprisingly, however, compound Vit II Z is a highly selective analog with unique biological activity.

Figure 5:
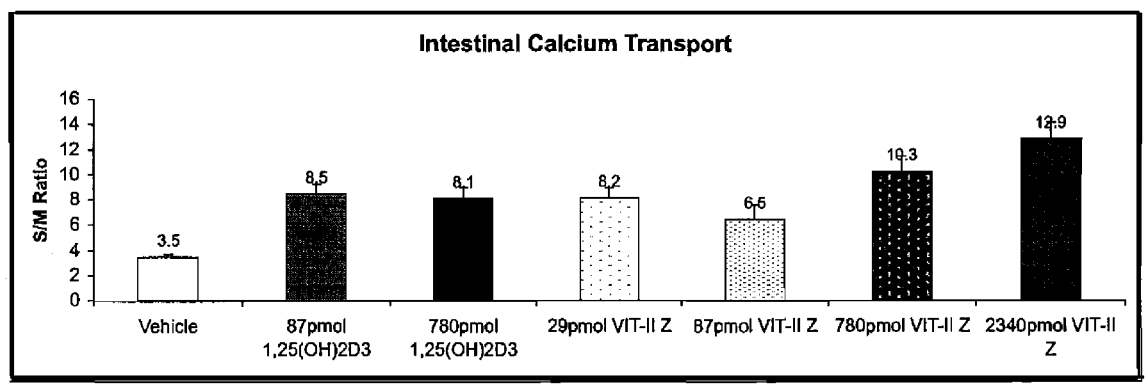

FIG. 5 shows that Vit II Z has significant ability to increase intestinal calcium transport activity in vivo, in a dose dependent manner, and it clearly has about the same or equal activity as compared to that of 1,25-dihydroxyvitamin $D_3$ (1,25 $(OH)_2D_3$), the natural hormone, in stimulating intestinal calcium transport. Vit II Z stimulated intestinal calcium transport as potently as 1,25$(OH)_2D_3$.

Figure 4:
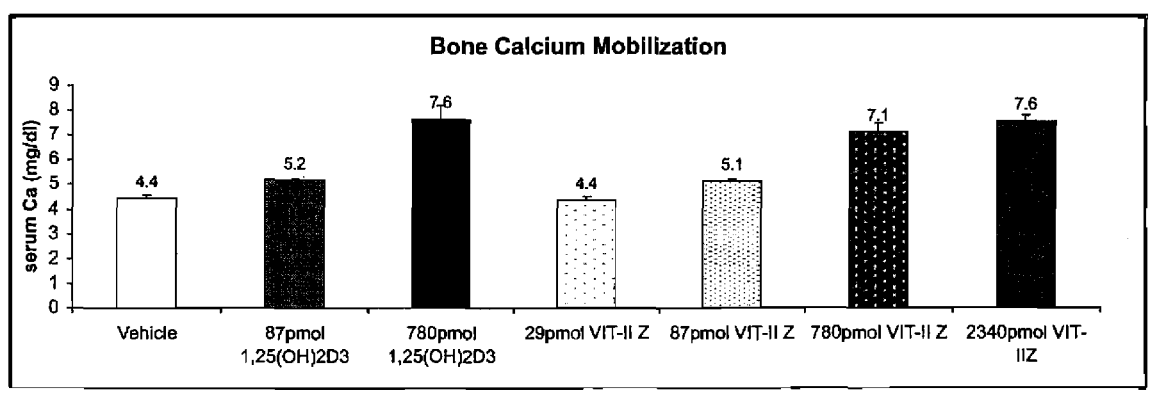

FIG. 4 demonstrates that Vit II Z also has significant bone calcium mobilization activity, as compared to 1,25$(OH)_2D_3$. Vit II Z has about the same or equal bone calcium mobilization activity compared to 1,25$(OH)_2D_3$.

FIGS. 4 and 5 thus illustrate that Vit II Z may be characterized as having significant calcemic activity.

Figure 2:
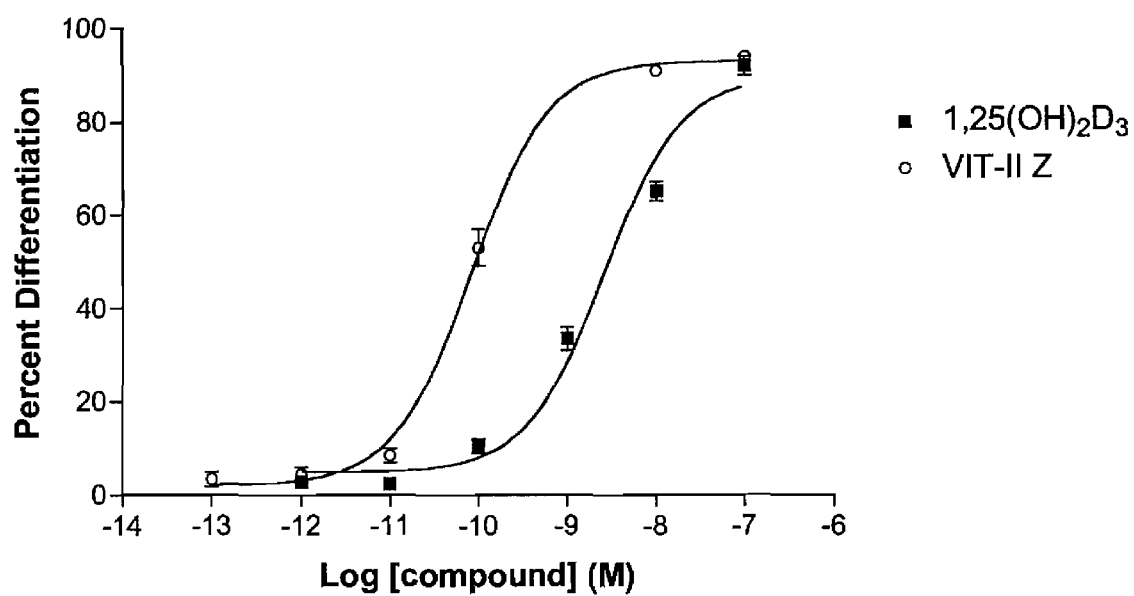

FIG. 2 illustrates that Vit II Z is about 25 times more potent than 1,25$(OH)_2D_3$ on HL-60 cell differentiation, i.e. causing the differentiation of HL-60 cells into monocytes, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
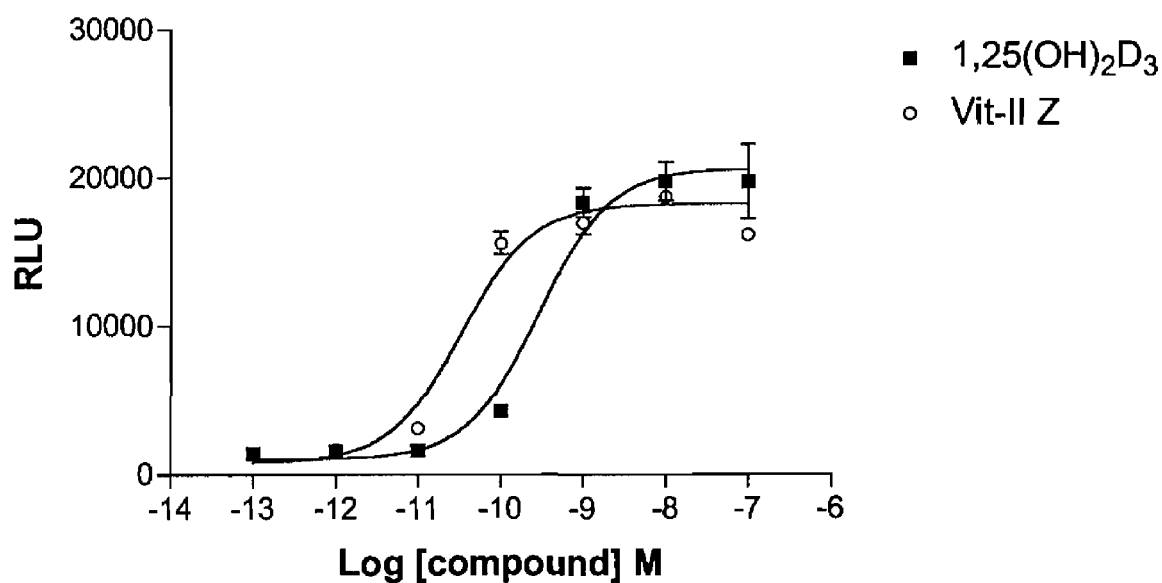

FIG. 3 illustrates that in bone cells the compound Vit II Z is one log, i.e. 10 times, more potent than 1,25$(OH)_2D_3$ in increasing transcription of the 24-hydroxylase gene. This result, together with the cell differentiation activity of FIG. 2, suggests that Vit II Z will be very effective in psoriasis because it has direct cellular activity in causing cell differentiation, gene transcription, and in suppressing cell growth. These data also indicate that Vit II Z may have significant activity as an anti-cancer agent, especially against leukemia, colon cancer, breast cancer, skin cancer and prostate cancer.

The strong activity of Vit II Z on HL-60 differentiation suggests it will be active in suppressing growth of parathyroid glands and in the suppression of the preproparathyroid gene.

Experimental Methods

Vitamin D Receptor Binding
Test Material
Protein Source
Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet +AEK oil for one week followed by Diet 11 (0.02% Ca) +AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

Summary of Biological Findings. This compound binds the VDR with nearly the same affinity as the native hormone, but displays approximately 25 times greater cell differentiation activity and more than 10 times in vitro gene transcription activity compared to 1,25$(OH)_2D_3$. In vivo this compound exhibits about the same or equal bone calcium mobilization and intestinal calcium transport activities compared to the native hormone making this compound a potentially valuable agent for the treatment of such diseases as cancer, renal osteodystrophy, autoimmune diseases, skin conditions, and psoriasis. While this compound is significantly more potent compared to 1,25$(OH)_2D_3$ in vitro, it shows similar calcium transport and calcium mobilizing activities in vivo compared to the native hormone. Due to the noticeably more potent cell differentiation and transcription activities and similar potency on tissue activities that raise blood calcium, this compound is likely to have a larger safety window than the native hormone. Vit II Z might not only be useful in the treatment of the above listed diseases, but also in the prevention of the above listed diseases.

VDR binding, HL60 cell differentiation, and transcription activity. Vit II Z ($K_i$=2×10$^{-10}$M) is almost as active as the natural hormone 1α,25-dihydroxyvitamin $D_3$ ($K_i$=4×10$^{-11}$M) in its ability to compete with [$^3$H]-1,25$(OH)_2D_3$ for binding to the full-length recombinant rat vitamin D receptor (FIG. 1). Vit II Z displays about 25 times greater activity ($EC_{50}$=8×10$^{-11}$M) in its ability (efficacy or potency) to promote HL-60 cell differentiation as compared to 1α,25-dihydroxyvitamin $D_3$ ($EC_{50}$=2×10$^{-9}$M) (See FIG. 2). Also, compound Vit II Z ($EC_{50}$=3×10$^{-11}$M) has more than 10 times greater transcriptional activity in bone cells than 1α,25-dihydroxyvitamin $D_3$ ($EC_{50}$=2×10$^{-10}$M) (See FIG. 3). These results suggest that Vit II Z will be very effective in psoriasis because it has direct cellular activity in causing cell differentiation, gene transcription, and in suppressing cell growth. These data also indicate that Vit II Z will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of Vit II Z and 1,25$(OH)_2D_3$ in intestine and bone were tested. As expected, the native hormone (1,25$(OH)_2D_3$) increased serum calcium levels at all dosages (FIG. 4). The study reported in FIG. 4 shows that Vit II Z has significant activity in mobilizing calcium from bone. Administration of Vit II Z at 87 pmol/day and at 780 pmol/day for 4 consecutive days resulted in mobilization of bone calcium activity that was about the same as or equal to the activity of 1,25(OH)$_2$D$_3$, and increasing the amount of Vit II Z to 2340 pmol/day was without any substantial additional effect.

Intestinal calcium transport was evaluated in the same groups of animals using the everted gut sac method (FIG. 5). These results show that the compound Vit II Z promotes intestinal calcium transport when administered at 29 pmol/day, and its activity is about the same as or equal to 1,25(OH)$_2$D$_3$ which also provides a significant increase at the tested doses. It was only when 2340 pmol/day of Vit II Z was administered that very significant intestinal calcium transport activity was recorded. Thus, it may be concluded that Vit II Z has essentially similar intestinal calcium transport activity at the recommended lower doses to that of 1,25(OH)$_2$D$_3$.

These results illustrate that Vit II Z is an excellent candidate for numerous human therapies as described herein, and that it may be particularly useful in a number of circumstances such as suppression of secondary hyperparathyroidism of renal osteodystrophy, autoimmune diseases, cancer, numerous types of skin conditions, and psoriasis. Vit II Z is an excellent candidate for treating psoriasis because: (1) it has significant VDR binding, transcription activity and cellular differentiation activity; (2) it has little hypercalcemic liability at relatively low doses, unlike 1,25(OH)$_2$D$_3$; and (3) it is easily synthesized. Since Vit II Z has significant binding activity to the vitamin D receptor, but has relatively low potency to raise blood serum calcium, it may also be particularly useful for the treatment of secondary hyperparathyroidism of renal osteodystrophy.

These data also indicate that the compound Vit II Z of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound Vit II Z of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I, particularly Vit II Z, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly Vit II Z, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly Vit II Z, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the compounds I, particularly Vit II Z, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds I, particularly Vit II Z, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly Vit II Z, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

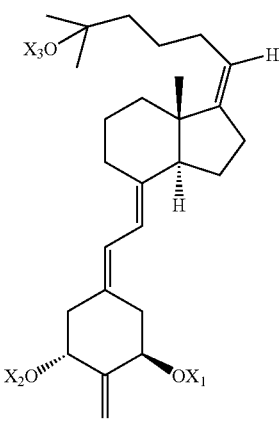

I where $X_1$, $X_2$ and $X_3$, which may be the same or different, are each selected from hydrogen or a hydroxy-protecting group.

2. The compound of claim 1 wherein $X_3$ is hydrogen.

3. The compound of claim 1 wherein $X_1$ is hydrogen.

4. The compound of claim 1 wherein $X_1$, $X_2$ and $X_3$ are all t-butyldimethylsilyl.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 μg to about 1000 μg per gram of composition.

7. The pharmaceutical composition of claim 5 wherein said effective amount comprises from about 0.1 μg to about 500 μg per gram of composition.

8. 2-methylene-(17Z)-17(20)-dehydro-19,21-dinor-1α,25-dihydroxyvitamin $D_3$ having the formula:

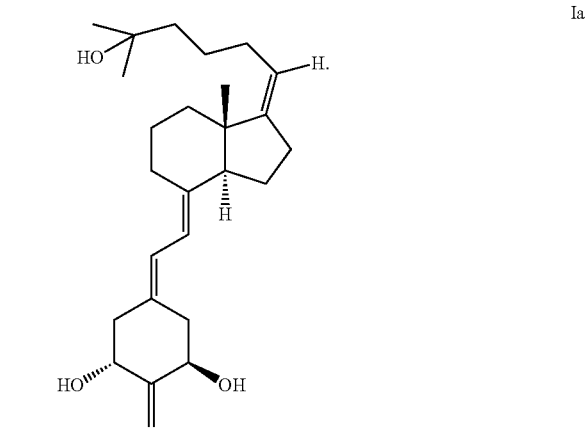

Ia

9. A pharmaceutical composition containing an effective amount of 2-methylene-(17Z)-17(20)-dehydro-19,21-dinor-1α,25-dihydroxyvitamin $D_3$ together with a pharmaceutically acceptable excipient.

10. The pharmaceutical composition of claim 9 wherein said effective amount comprises from about 0.01 μg to about 1000 μg per gram of composition.

11. The pharmaceutical composition of claim 9 wherein said effective amount comprises from about 0.1 μg to about 500 μg per gram of composition.

12. A method of treating psoriasis comprising administering to a subject with psoriasis an effective amount of a compound having the formula:

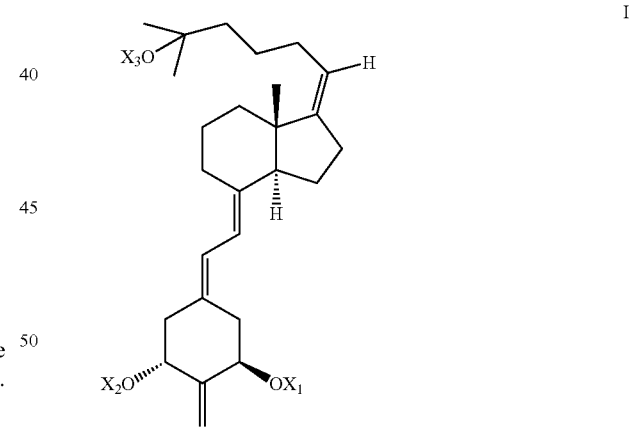

I where $X_1$, $X_2$ and $X_3$ which may be the same or different, are each selected from hydrogen or a hydroxy-protecting group.

13. The method of claim 12 wherein the compound is administered orally.

14. The method of claim 12 wherein the compound is administered parenterally.

15. The method of claim 12 wherein the compound is administered transdermally.

16. The method of claim 12 wherein the compound is administered topically.

17. The method of claim 12 wherein the compound is administered rectally.

18. The method of claim 12 wherein the compound is administered nasally.

19. The method of claim 12 wherein the compound is administered sublingually.

20. The method of claim 12 wherein the compound is administered in a dosage of from about 0.01 μg/day to about 1000 μg/day.

21. The method of claim 12 wherein the compound is 2-methylene-(17Z)-17(20)-dehydro-19,21-dinor-1α,25-dihydroxyvitamin D₃ having the formula:

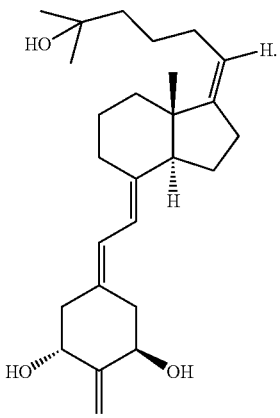

Ia

22. A method of treating a disease selected from the group consisting of leukemia, colon cancer, breast cancer, skin cancer or prostate cancer comprising administering to a subject with said disease an effective amount of a compound having the formula:

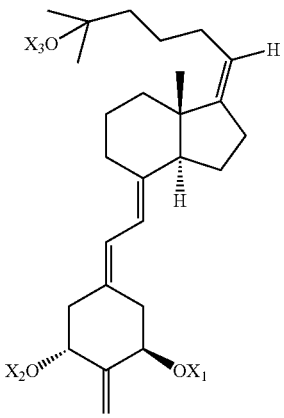

I where X₁, X₂ and X₃ which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 μg/day to about 1000 μg/day.

30. The method of claim 22 wherein the compound is 2-methylene-(17Z)-17(20)-dehydro-19,21-dinor-1α,25-dihydroxyvitamin D₃ having the formula:

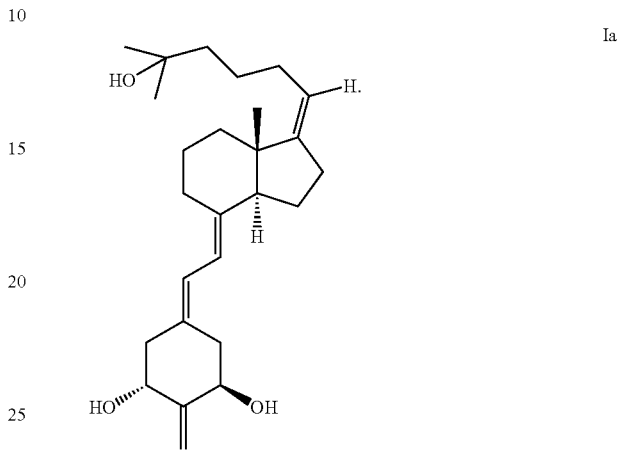

Ia

31. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

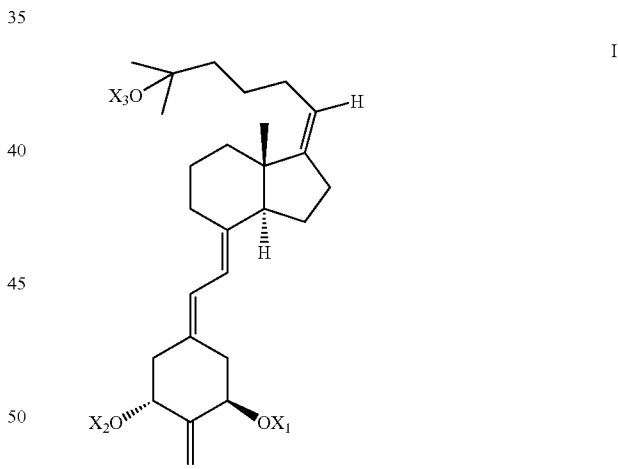

I where X₁, X₂ and X₃ which may be the same or different, are each selected from hydrogen or a hydroxy-protecting group.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 wherein the compound is 2-methylene-(17Z)-17(20)-dehydro-19,21-dinor-1α,25-dihydroxyvitamin D₃ having the formula:

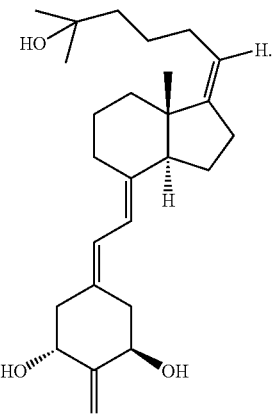

Ia

40. A method of treating an inflammatory disease selected from the group consisting of rheumatoid arthritis, asthma, and inflammatory bowel diseases, comprising administering to a subject with said disease an effective amount of a compound having the formula:

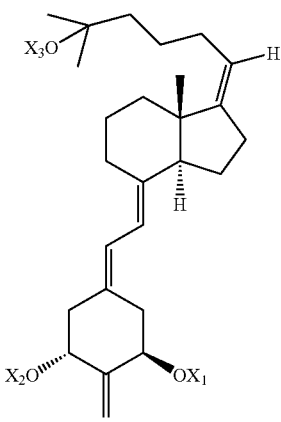

I where $X_1$, $X_2$ and $X_3$, which may be the same or different, are each selected from hydrogen or a hydroxy-protecting group.

41. The method of claim 40 wherein the compound is administered orally.

42. The method of claim 40 wherein the compound is administered parenterally.

43. The method of claim 40 wherein the compound is administered transdermally.

44. The method of claim 40 wherein the compound is administered rectally.

45. The method of claim 40 wherein the compound is administered nasally.

46. The method of claim 40 wherein the compound is administered sublingually.

47. The method of claim 40 wherein the compound is administered in a dosage of from about 0.01 μg/day to about 1000 μg/day.

48. The method of claim 40 wherein the compound is 2-methylene-(17Z)-17(20)-dehydro-19,21-dinor-1α,25-dihydroxyvitamin D₃ having the formula:

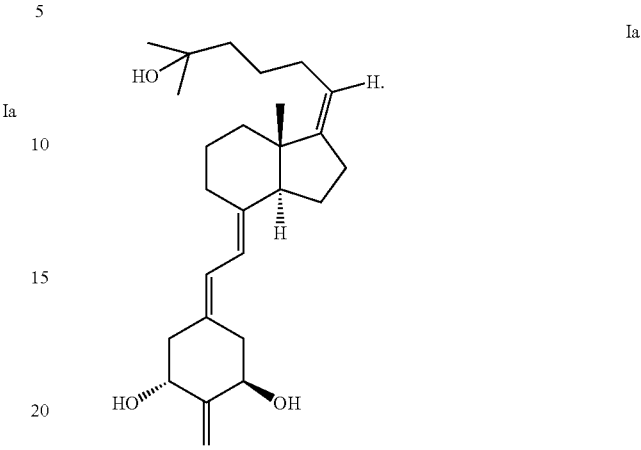

Ia

49. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

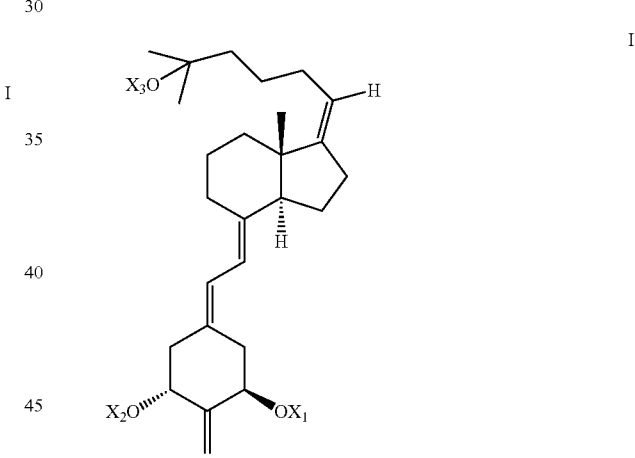

I where $X_1$, $X_2$ and $X_3$ which may be the same or different, are each selected from hydrogen or a hydroxy-protecting group.

50. The method of claim 49 wherein the compound is administered orally.

51. The method of claim 49 wherein the compound is administered parenterally.

52. The method of claim 49 wherein the compound is administered transdermally.

53. The method of claim 49 wherein the compound is administered topically.

54. The method of claim 49 wherein the compound is administered rectally.

55. The method of claim 49 wherein the compound is administered nasally.

56. The method of claim 49 wherein the compound is administered sublingually.

57. The method of claim 49 wherein the compound is administered in a dosage of from about 0.01 μg/day to about 1000 μg/day.

58. The method of claim 49 wherein the compound is 2-methylene-(17Z)-17(20)-dehydro-19,21-dinor-1α,25-dihydroxyvitamin D₃ having the formula:

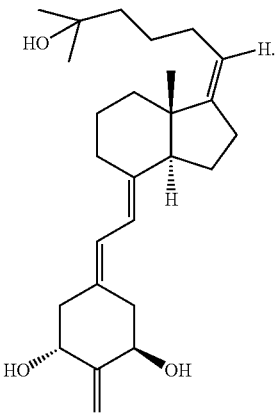

Ia

59. A method of treating renal osteodystrophy comprising administering to a subject with renal osteodystrophy an effective amount of a compound having the formula:

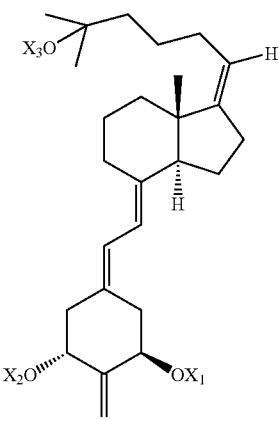

I where $X_1$, $X_2$ and $X_3$, which may be the same or different, are each selected from hydrogen or a hydroxy-protecting group.

60. The method of claim 59 wherein the compound is administered orally.

61. The method of claim 59 wherein the compound is administered parenterally.

62. The method of claim 59 wherein the compound is administered transdermally.

63. The method of claim 59 wherein the compound is administered rectally.

64. The method of claim 59 wherein the compound is administered nasally.

65. The method of claim 59 wherein the compound is administered sublingually.

66. The method of claim 59 wherein the compound is administered in a dosage of from about 0.01 μg/day to about 1000 μg/day.

67. The method of claim 59 wherein the compound is 2-methylene-(17Z)-17(20)-dehydro-19,21-dinor-1α,25-dihydroxyvitamin D₃ having the formula:

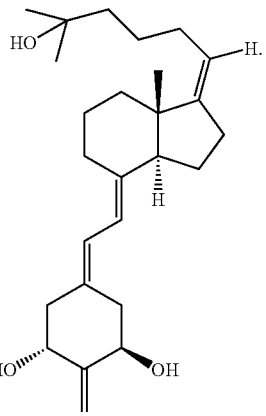

Ia

68. A method of treating obesity of an animal, inhibiting adipocyte differentiation, inhibiting SCD-1 gene transcription, and/or reducing body fat in an animal comprising administering to an animal in need thereof an effective amount of a compound having the formula:

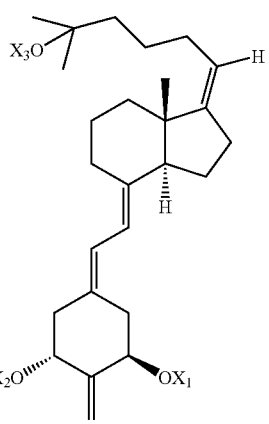

I where $X_1$, $X_2$ and $X_3$, which may be the same or different, are each selected from hydrogen or a hydroxy-protecting group.

69. The method of claim 68 wherein the compound is administered orally.

70. The method of claim 68 wherein the compound is administered parenterally.

71. The method of claim 68 wherein the compound is administered transdermally.

72. The method of claim 68 wherein the compound is administered rectally.

73. The method of claim 68 wherein the compound is administered nasally.

74. The method of claim 68 wherein the compound is administered sublingually.

75. The method of claim 68 wherein the compound is administered in a dosage of from about 0.01 µg/day to about 1000 µg/day.

76. The method of claim 68 wherein the compound is 2-methylene-(17Z)-17(20)-dehydro-19,21-dinor-1α,25-dihydroxyvitamin $D_3$ having the formula:

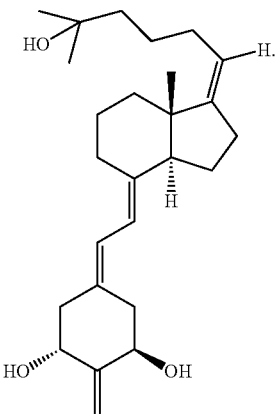

Ia

77. The method of claim 68 wherein the animal is a human.

78. The method of claim 68 wherein the animal is a domestic animal.

79. The method of claim 68 wherein the animal is an agricultural animal.

* * * * *